US006537222B1

(12) United States Patent
Clark et al.

(10) Patent No.: US 6,537,222 B1
(45) Date of Patent: *Mar. 25, 2003

(54) METHODS FOR THE DETECTION OF CONTRAST AGENTS IN ULTRASONIC IMAGING

(75) Inventors: David W. Clark, Windham, NH (US); Patrick G. Rafter, Woburn, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 08/920,057

(22) Filed: Aug. 26, 1997

(51) Int. Cl.[7] ................................................. A61B 8/00
(52) U.S. Cl. ..................................................... 600/458
(58) Field of Search ................................. 600/455, 443, 600/458; 424/9.52

(56) References Cited

U.S. PATENT DOCUMENTS

| | | | | |
|---|---|---|---|---|
| 4,442,843 A | * | 4/1984 | Rasor et al. | 600/458 X |
| 4,884,448 A | * | 12/1989 | Ogawa et al. | 600/455 X |
| 5,220,923 A | * | 6/1993 | Hagiwara et al. | 600/455 |
| 5,255,683 A | * | 10/1993 | Monaghan | 600/458 |
| 5,311,870 A | * | 5/1994 | Fukukita et al. | 600/455 |
| 5,456,257 A | * | 10/1995 | Johnson et al. | 600/458 |
| 5,526,816 A | * | 6/1996 | Arditi | 600/458 |
| 5,577,505 A | * | 11/1996 | Brock-Fisher et al. | 600/458 |
| 5,632,277 A | * | 5/1997 | Chapman et al. | 600/443 |
| 5,706,819 A | * | 1/1998 | Hwang et al. | 600/458 |

OTHER PUBLICATIONS

Powers, J.E. et al "OTS Diagnostic Imaging w/Contrast Agents" EP 0770352 Published May 2, 1997.*

* cited by examiner

*Primary Examiner*—Francis J. Jaworski
(74) *Attorney, Agent, or Firm*—John Vodopia

(57) ABSTRACT

Quadrature demodulation apparatus and method for detecting a contrast agent in an ultrasonic echographic system, including an in phase/quadrature demodulator for determining the resolved complex real and imaginary in phase and quadrature components of return signals and a contrast agent detector determining the complex difference between first and second return signals. The detector is implemented as a magnitude of difference detector determining the magnitude of the complex difference of pairs of first and second return signals wherein the real and imaginary components of the return signals, including magnitude and phase information, are used to determine the magnitude of the complex difference between first and second return signals. The detector is also implemented as an asymmetrical weighting detector resolving the complex difference between first and second return signals into components in phase with and orthogonal to the second signal and weighting the magnitudes of in phase and orthogonal components of the complex difference and indicating a contrast agent present when the combination of differently weighted component exceeds the corresponding threshold value. The detector is also implemented as an extrapolation detector for receiving three successive return signals along each line wherein the second return signal and a third return signal are used to extrapolate what the first return signal would have been without the contrast agent component and to generate a decision threshold that is compared to the complex difference between the actual first return signal and the extrapolated first return signal.

41 Claims, 6 Drawing Sheets

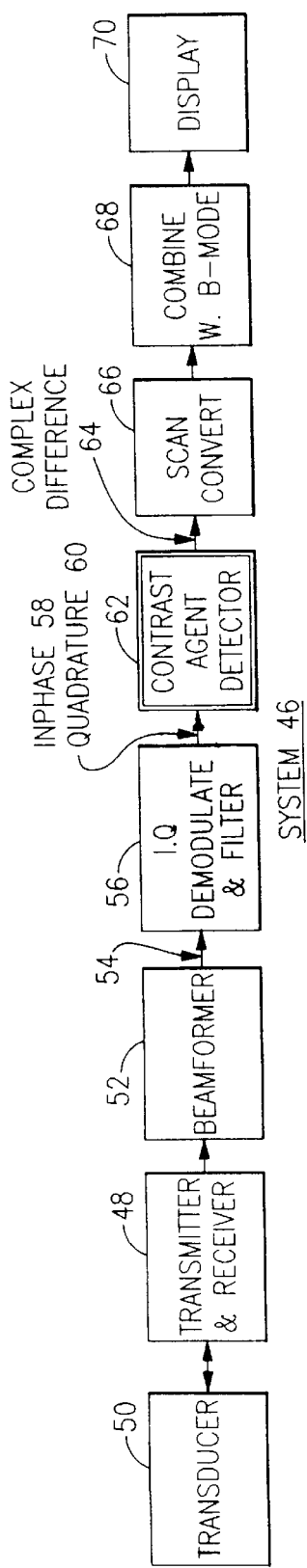
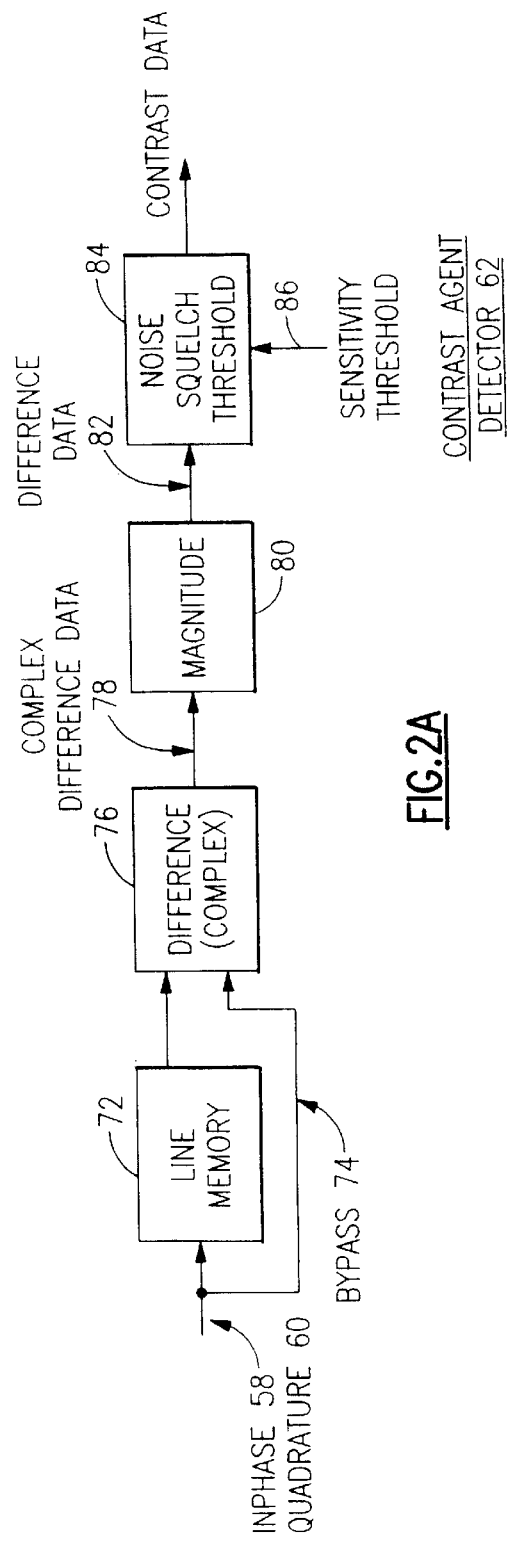

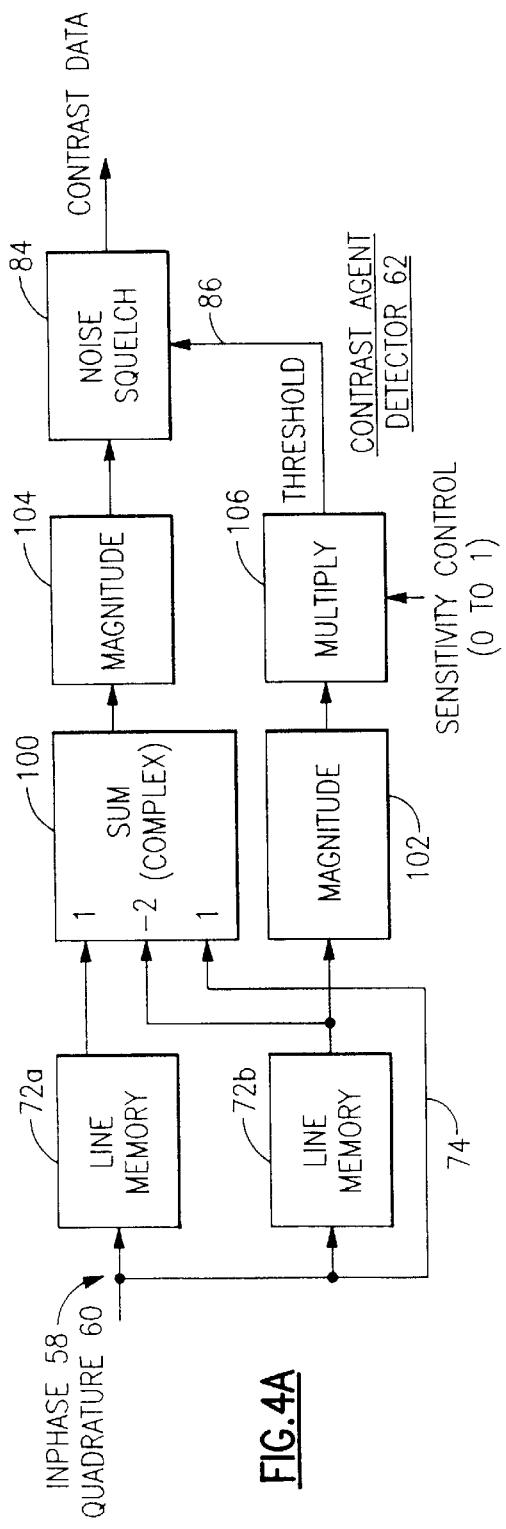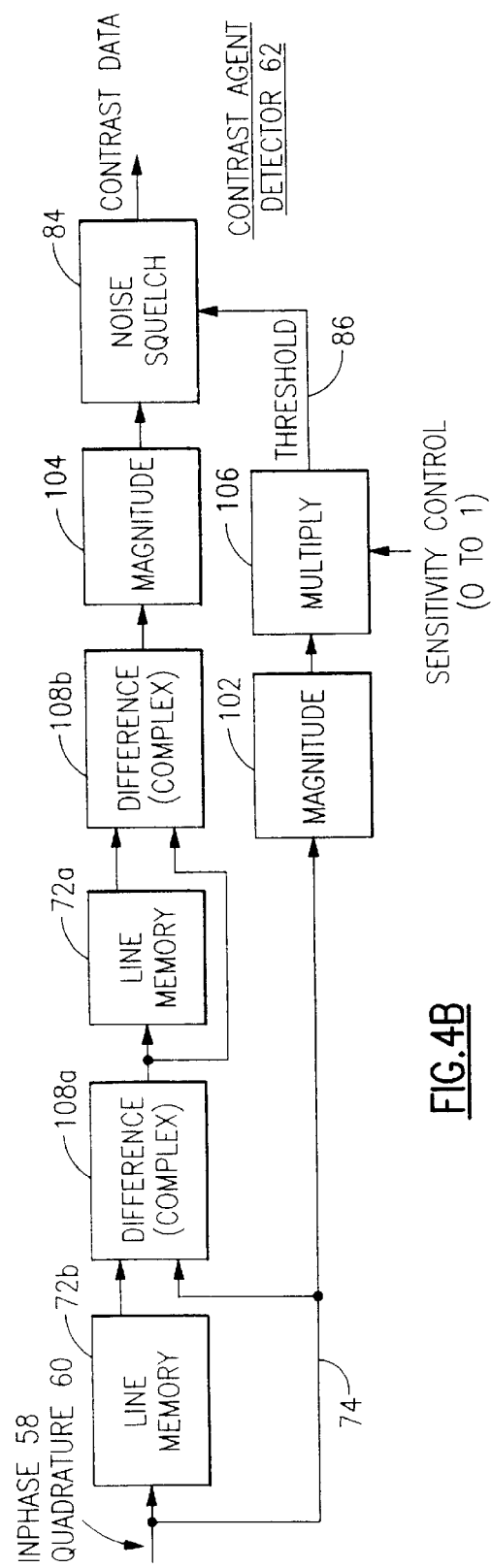

| | TISSUE ECHO POWER LEVEL 5% PROBABILITY FALSE RESULT |
|---|---|
| A | −13.5 dB |
| B | −12.0 dB |
| C | −8.5 dB |
| D | −4.8 dB |
| E | −3.0 dB |
| F | +2.1 dB |
| G | +4.1 dB |
| H | +7.5 dB |

FIG.5I

METHODS FOR THE DETECTION OF CONTRAST AGENTS IN ULTRASONIC IMAGING

CROSS REFERENCES TO RELATED APPLICATIONS

1. Field of the Invention

The present invention relates to an improved apparatus and method for detecting contrast agents in ultrasonic imaging and, in particular, apparatus and methods for use of quadrature demodulation in detecting contrast agents.

2. Background of the Invention

Ultrasonic transducers and imaging systems are used in many medical applications and, in particular, for the non-invasive acquisition of images of organs and conditions within a patient, typical examples being the ultrasound imaging of fetuses and the heart. Such systems commonly use a linear or phased array transducer having multiple transmitting and receiving elements to transmit and receive narrowly focused and "steerable" beams, or "lines", of ultrasonic energy into and from the body. The received beams, or lines, are reflected from the body's internal structures and contain amplitude or phase information, or both, that is used to generate images of the body's internal structures.

A primary problem in ultrasonic imaging has been that many of the body's internal structures have similar characteristics as regards the reflection of ultrasonic energy, so that it is difficult to obtain as clear and detailed images as is desired of many of the structures, such as the muscles of the heart.

This problem led to the development of alternative methods for imaging certain of the body's structures, such as the blood vessels of the heart. One of the most common imaging techniques, for example, referred to as an angiogram, requires the injection of a radio-opaque dye into the vessels to image the blood vessels of the heart with x-rays. Such techniques, however, are invasive or are otherwise unsatisfactory. For example, the use of x-ray imaging carries the risk of potential injury from radiation and involves complex, expensive and hazardous equipment. Also, radio-opaque dyes are potentially toxic to at least some patients and are not broken down in the body but are flushed from the body by natural waste processes, often requiring hours to disappear from the body.

A more recent development has been ultrasonic imaging using contrast agents injected into the blood stream. Ultrasonic contrast agents are now commercially available and are essentially small bubbles of gas, such as air, formed by agitating a liquid or bubbling gas through a liquid, such as a saline solution or a solution containing a bubble forming compound, such as albumin. When insonicated, the bubbles resonate at their resonant frequency and at the second harmonic of their resonant frequency, thereby returning an enhanced signal at or around these frequencies and thereby providing an enhanced image of the liquid or tissue containing the contrast agent. It is also well known that the bubbles "disappear" when insonicated at a high enough power level and the current theory is that the insonication ruptures the bubble's shell, thereby allowing the gas to dissipate into the surrounding liquid or tissue.

The use of ultrasonic contrast agents is thereby advantageous in allowing enhanced imaging using ultrasonics rather than x-rays, thereby eliminating the radiation hazard and allowing the use of equipment that is significantly less expensive and hazardous to use. Also, the agents are non-toxic and dissolve relatively quickly into waste products, such as air and albumin, that are normally found in the body and that are themselves non-toxic. Further, the insonication of the agent in itself destroys the agent, so that the agent can effectively be "erased" during or after the imaging process.

There are, however, a number of persistent problems in ultrasonic imaging using contrast agents, many of which concern the detection of contrast agents in the tissues of interest and the measurement of contrast agent concentrations in the tissues of interest.

For example, many ultrasonic imaging systems using contrast agents generate the desired image from two or more successive returned signals wherein the first returned signal is the sum of a component due to the bubbles being destroyed by the insonication and other components from other sources, such as the tissue, clutter and bubbles that were not destroyed by the insonication. The second returned signal includes components from the other sources, such as the tissue, clutter and bubbles that were not destroyed, but does not have a component from the bubbles being destroyed by the insonication that generated the first returned signal. As a consequence, an image primarily representing the contrast agent, that is, the bubbles being destroyed by the insonication, and thus an enhanced image of the tissues containing the contrast agent, can be generated by subtracting the components of the second returned signal from the components of the first returned signal.

This method may also be used to determine the concentration of contrast agent in the tissues of interest by determining the change in the returned signals between the first and second or later returned, and is thereby useful in other applications. For example, the change in concentration of contrast agent in the tissues of interest may be used to determine the rate of perfusion, that is, blood flow, in the tissues of interest. In a further extension of this method, the difference in rate of perfusion between, for example, a ischemia infarction and the heart muscle tissues may be used to detect the boundaries between the ischemia infarction and surrounding muscle tissue and thereby to generate enhanced images of the heart.

In another example, the ability to control the concentration of contrast agent in a region of interest, for example, by selectably destroying contrast agent through controlled insonication, is a significant advantage because too high a concentration of contrast agent results in saturation and non-linear, flat images due to interference between the bubbles. Also, and as a related problem, a too high a concentration of contrast agent in regions between the transducer and the region of interest will result in a shadowing effect wherein the near region image return will shadow, that is, hide or at least degrade the image in the region of interest.

All of these techniques, however, require the detection of contrast agents in the tissues of interest, or the measurement of contrast agent concentrations in the tissues of interest.

Broadly, the two primary methods for determining the components in returned signals or the difference in components between successive returned signals are, first, simply measuring the amplitude of the returned signals, and, second, measuring the complex vector components, that is, the phasor components, of the returned signals, for example, by quadrature demodulation of the returned signals into their amplitude and phase components. Of these two methods, quadrature demodulation would be generally preferred, for example, as providing more complete and detailed information regarding the returned signals and thus potentially providing superior images.

In quadrature demodulation, however, the returned signal at any particular spatial location in the tissues of interest is generally a complex number, or phasor. That is, the first returned signal is the vector sum of a phasor component due to the bubbles being destroyed by the insonication and other phasor components from other sources, such as the tissue, clutter and bubbles that were not destroyed by the insonication. The second returned signal, in turn, includes phasor components from the other sources, such as the tissue, clutter and bubbles that were not destroyed, but does not have a phasor component from the bubbles being destroyed by the insonication that generated the first returned signal.

The phasor components of the second returned signal, however, will generally differ to a greater or lessor degree from the corresponding phasor components of the first returned signal because of blood, tissue or transducer motion. This difference will generally primarily appear as a phase rotation, and will generally be a relatively small fraction of a cycle because of the relative short time between transmit pulses, and thus between returned signals.

In addition, however, the burst bubble phasor component of the first returned signal will be uncorrelated in both magnitude and phase with the phasor components from other sources, such as the tissue, clutter and bubbles that were not destroyed, and can cause the returned signal to be larger or smaller in magnitude or advanced or retarded in phase, or any combination thereof, compared to what the returned signal would be without the component from bursting bubbles. As such, and although the expected value of the magnitude should be greater with the bursting bubble component than without, the actual value of the magnitude of the returned signal could be larger, the same as, or smaller than without the component from bursting bubbles, depending upon the relative phases of the signal components. Still further, the magnitude of the return signal will vary randomly due to "speckle" and noise, although the system noise component may be negligible in the case of bubbles perfusing in dense tissues.

Any method for detecting one speckly signal in the presence of another uncorrelated speckly signal or detecting one variable magnitude signal by comparison to another variable magnitude signal by thresholding will therefore provide an uncertain result at the yes/no boundary in the decision process.

Because of these problems, many systems of the prior art use only the difference in magnitude between the signals, for example, detecting only the magnitude of the second harmonic of the returned signal as the second harmonic component is primarily due to the contrast agent. Certain of the systems of the prior art have even explicitly rejected the use of phase dependent information, stating that not using phase related information is an essential key to the detection of contrast agents because it allows the destruction of bubbles to be distinguished from echo change due to motion of the tissue or the transducer. The systems of the prior art have also been based on the principle that detection thresholds are not dependent upon any signal characteristic.

There are grounds to believe, however, as discussed in the following description of the invention, that the systems of the prior art using these approaches are incorrect in these assumptions and that they accordingly do not provide optimum results.

The present invention therefore provides a solution to these and other problems of the prior art by providing improved methods for the use of contrast agents.

SUMMARY OF THE INVENTION

The present invention is directed to an apparatus and a method for using quadrature demodulation to detect a contrast agent in an ultrasonic echographic system which receives ultrasonic return signals containing components due to tissues and possibly due to a contrast agent wherein each return signal represents an image along a single receiving line of a transducer. According to the present invention, a quadrature demodulation contrast agent detector includes an in phase/quadrature demodulator for determining the in phase and quadrature components of each return signal, wherein the in phase and quadrature components of each return signal are the resolved complex components, real and imaginary, of each return signal that are respectively in phase with and in quadrature phase with a reference signal, and a contrast agent detector for determining the complex difference between a first return signal and a second return signal and generating a complex difference value representing the complex difference.

The contrast agent detector of the present invention may be embodied in a number of implementations, one of which is a magnitude of difference detector for determining the magnitude of the complex difference of pairs of a first return signal and a second return signal wherein both the real and imaginary components of the return signals, which include both magnitude and phase information, are used to determine the magnitude of the complex difference between the first and second return signals.

The magnitude of difference contrast agent detector includes a complex difference calculator for determining the difference between the in phase and quadrature components of the first and second return signals and generating a complex difference value for each pair of first and second return signals wherein each complex difference value will have an in phase component and a quadrature component representing the complex difference between the real and imaginary components of the first and second return signals. A magnitude resolver is connected from the complex difference calculator for resolving the in phase and quadrature components of the complex difference value for each pair of first and second return signals and generating a difference magnitude value representing the magnitude of the complex difference between the real and imaginary components of each pair of first and second return signals. A threshold comparator then compares the value of the difference magnitude value of each pair of first and second return signals with a predetermined, selectable threshold value and generates an output representing a contrast agent component when a difference magnitude value exceeds the threshold value.

The magnitude of difference contrast agent detector may also include a memory for receiving and storing the in phase and quadrature components of the first return signal and providing the in phase and quadrature components of the first return signal to the complex difference calculator, and a bypass connected around the memory for providing the in phase and quadrature components of the second return signal to the complex difference calculator concurrently with the stored in phase and quadrature components of the first return signal.

The magnitude of difference contrast agent detector may also be implemented with a second magnitude resolver for receiving the in phase and quadrature components of the second return signal and determining a second magnitude value representing the magnitude of the second return signal, including both contributions from the tissue and from other causes and sources other than the contrast agent, and a multiplier for receiving the second magnitude value and multiplying the second magnitude value by a predetermined value to generate a threshold value representing a proportion of the signal magnitude from sources other than the contrast agent.

The magnitude of difference contrast agent detector may further be implemented with a second magnitude resolver for receiving the in phase and quadrature components of the second return signal and determining a second magnitude value representing the magnitude of the second return signal, including both contributions from the tissue and from other causes and sources other than the contrast agent, and a divider for receiving the difference magnitude value and the second magnitude value and dividing the value of the difference magnitude value by the value of the second magnitude value to generate the threshold value thereby scaling the difference magnitude value relative to a selectable fixed threshold value to provide a variable threshold value relative to the magnitude of the second return signal, including both contributions from the tissue and from other causes and sources other than the contrast agent.

It is known that the change in a background echo, that is, in everything except the bursting bubbles, is primarily a phase rotation. For this reason, and in yet a further alternate embodiment, the quadrature demodulation contrast agent detector may be implemented as an asymmetrical weighting detector for resolving the complex difference between first and second return signals into components in phase with and orthogonal to the second signal and weighting these two components differently for generating corresponding threshold values for the in phase and orthogonal components of the complex difference between the first and second return signals wherein a contrast agent is indicated when the weighted combination of the in phase or orthogonal components exceeds the corresponding threshold value.

The asymmetrical weighting contrast agent detector includes a complex difference calculator for determining the difference between the in phase and quadrature components of the first and second return signals and generating a complex difference value for each pair of first and second return signals wherein each complex difference value has a real component value which represents the difference between the real components of the first and second return signals and an imaginary component value which represents the difference between the imaginary components of the first and second return signals. A magnitude resolver is connected from the complex difference calculator for receiving the second return signal and generating a value representing the magnitude of the second return signal, and the detector further includes a first divider for receiving the complex difference value and dividing the real and imaginary component values by the value representing the magnitude of the second return signal and generating a scaled complex difference signal representing the complex difference between the first and second return signals, and a second divider for receiving the second return signal and the value representing the magnitude of the second return signal and dividing the second return signal by the value representing the magnitude of the second return signal for generating a unit magnitude signal representing the real and imaginary components of the second return signal and in phase with the second return signal. A conjugate multiplier then receives the outputs of the first and second dividers and multiplies the scaled complex difference signal by the conjugate of the unit magnitude signal to generate a scaled complex difference signal rotated in the complex plane and having a real component representing the scaled complex difference in phase with the second return signal and an imaginary component orthogonal to the second return signal. An asymmetric weighted combiner then receives the rotated scaled complex difference signal, weights the real and imaginary components of the rotated scaled complex difference signal with corresponding coefficients, and combines the weighted real and imaginary components to generate a combined magnitude value. A threshold comparator then compares the combined magnitude value with a predetermined, selectable threshold value and generates an output representing a contrast agent component when a difference magnitude value exceeds the threshold value.

The asymmetrical weighting detector may also include a memory for receiving and storing the in phase and quadrature components of the first return signal and providing the in phase and quadrature components of the first return signal to the complex difference calculator, and a bypass connected around the memory for providing the in phase and quadrature components of the second return signal to the complex difference calculator, to the magnitude resolver and to the first divider concurrently with the stored in phase and quadrature components of the first return signal.

In another alternate embodiment, the asymmetric weighted combiner may weight the real and imaginary components of the rotated scaled complex difference signal by separately squaring and adding the real and imaginary components with different weighting coefficients so that the combined magnitude value that is compared to the threshold defines an elliptical threshold in the complex plane.

In yet another alternate embodiment, the asymmetric weighted combiner may weight the absolute value of the real and imaginary components of the rotated scaled complex difference signal by adding the real and imaginary components with corresponding weighting coefficients so that the combined magnitude value that is compared to the threshold defines a rhomboidal threshold in the complex plane.

In another alternate embodiment, the asymmetric weighted combiner weights the real and imaginary components of the rotated scaled complex difference signal by separately weighting the real and imaginary components with corresponding coefficients and comparing the greater of the weighted real and imaginary components with the threshold so that the combined magnitude value that is compared to the threshold defines a rectangular threshold in the complex plane.

In yet another embodiment, the contrast agent detector may be implemented as an extrapolation detector for receiving three successive return signals along each receiving line wherein the second return signal and a third return signal are used to extrapolate what the first return signal would have been without the contrast agent component and to generate a decision threshold that is compared to the complex difference between the actual first return signal and the extrapolated first return signal.

According to the present invention, the extrapolation contrast agent detector includes a complex summer for receiving the first, second and third return signals and performing a complex phasor summation of the first, second and third return signals to generate a complex sum that represents the difference between the actual first return signal and an extrapolated first return signal generated from the second and third return signals and without a contribution from a contrast agent, a first magnitude resolver for receiving the complex and generating a value representing the magnitude of the complex sum, and a second magnitude resolver for receiving the second return signal and generating a value representing the magnitude of the second return signal. A multiplier receives the value representing the magnitude of the second return signal and multiplies the value representing the magnitude of the second return signal by a coefficient to generate a threshold value, and a threshold comparator for receives the threshold value and the complex sum representing the difference between the actual first return signal and the extrapolated first return signal and generates an output representing whether the magnitude of the complex sum exceeds the threshold value.

In one embodiment of the extrapolation contrast agent detector, the complex summer generates a complex sum of the first, second and third return signals wherein the first and third return signals are summed with multipliers of +1 and the second return signal is summed with a −2 multiplier. Further in this embodiment, the extrapolation detector may further include a first memory and a second memory, each for receiving and storing the first, second and third return signals, wherein the first memory provides the first return signal to the complex summer and the second memory provides the second return signal to the complex summer and to the first magnitude resolver, and a bypass for providing the third return signal to the complex summer.

In an alternate embodiment, the extrapolation contrast agent detector may include a first complex difference calculator for generating a first complex difference between the first and second return signals and a second complex difference calculator for generating a second complex difference representing the complex difference between two successive first complex differences, wherein the second complex difference thereby represents the complex difference between the actual first return signal and an extrapolated first return signal generated from the second and third return signals and not including a contrast agent component. This embodiment further includes a magnitude resolver for receiving the second return signal and generating a value representing the magnitude of the second return signal, a multiplier for receiving the value representing the magnitude of the second return signal and multiplying the value representing the magnitude of the second return signal by a coefficient to generate a threshold value, and a threshold comparator for receiving the threshold value and the complex sum representing the difference between the actual first return signal and the extrapolated first return signal and generating an output representing whether the complex sum exceeds the threshold value.

Finally, in this embodiment the extrapolation contrast agent detector may further include a first memory for storing the first return signal, the second return signal and the third return signal and providing the first return signal to the first complex difference calculator, a first bypass for providing the second return signal to the first difference calculator in conjunction with the first return signal from the first memory and the second return signal to the magnitude resolver, a second memory for storing the first complex difference between the first and second return signals and the second complex difference representing the complex difference between the second and third return signals, and a second bypass for providing the second complex difference between the second return signal and the third return signal to the second complex difference calculator in conjunction with the first complex difference between the first return signal and the second return signal from the second memory.

In yet other embodiments of the extrapolation contrast agent detector, the quadrature demodulation contrast agent detector is expanded to deal with more than three return signals by means of a complex summer for receiving the first return signal and n subsequent successive return signals and performing a complex phasor summation of the first return signal and the n subsequent successive return signals to generate a complex sum that represents the difference between the actual first return signal and an extrapolated first return signal generated from the n subsequent successive return signals and without a contribution from a contrast agent. A first magnitude resolver then receives the complex sum and generates a value representing the magnitude of the complex sum while a second magnitude resolver for receives the n subsequent successive return signals and generates a value representing the magnitude of the n subsequent successive return signals. A multiplier receives the value representing the magnitude of the n subsequent successive return signals and multiplies the value representing the magnitude of the n subsequent successive return signals by a coefficient to generate a threshold value, and a threshold comparator receives the threshold value and the complex sum representing the difference between the actual first return signal and the extrapolated first return signal and generates an output representing whether the complex sum exceeds the threshold value.

Further according to this embodiment of the extrapolation contrast agent detector, the first and n subsequent successive return signals in a given direction are interleaved with a first and n subsequent successive return signals in at least one other given direction and an extrapolated first return signal is generated for each given direction.

Other features, objects and advantages of the present invention will be understood by those of ordinary skill in the art after reading the following descriptions of a present implementation of the present invention, and after examining the drawings, wherein:

BRIEF DESCRIPTION OF THE DRAWINGS

FIG. 1 is a block diagram of an exemplary ultrasonic echographic system incorporating the present invention;

FIG. 2A is a block diagram of a contrast agent detector of the present invention implementing the magnitude of differences method of detection;

FIGS. 4A and 4B are block diagrams of a contrast agent detector of the present invention implementing the extrapolation method of detection; and, FIGS. 5A through 5I are illustrations of the contrast agent detection results obtained by a system implementing the present invention and a system of the prior art.

DESCRIPTION OF A PRESENTLY PREFERRED EMBODIMENT

Figure 2B:
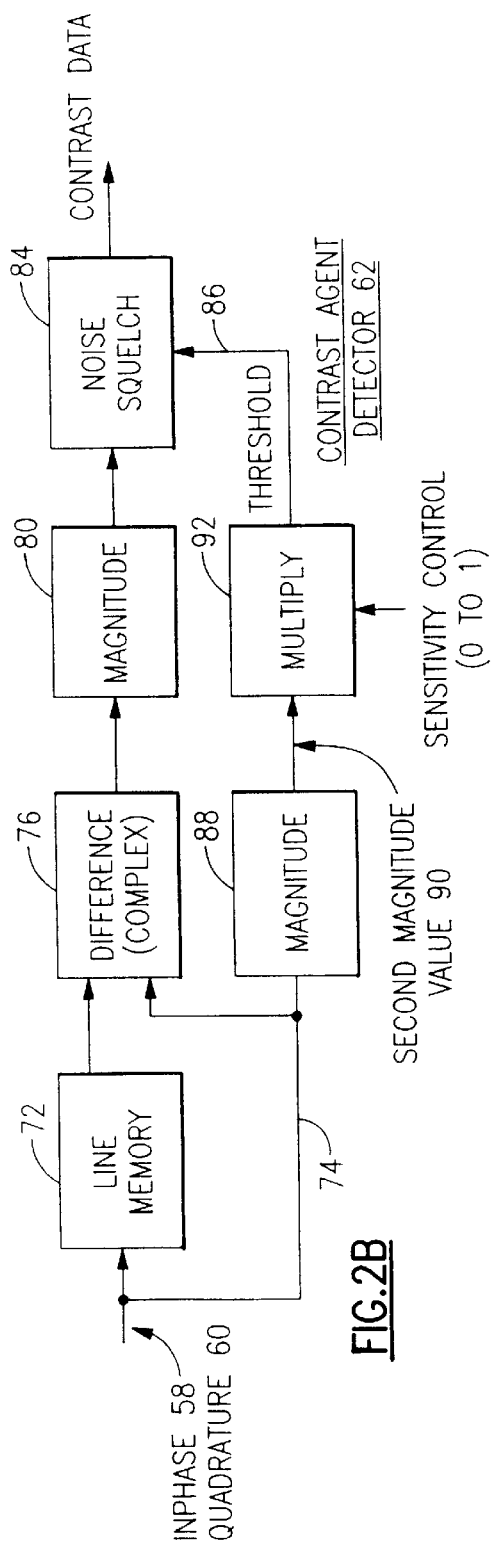
FIGS. 2B and 2C are block diagrams of alternate embodiments of the contrast agent detector shown in FIG. 2A.

The following will first describe a generalized ultrasonic echographic system in which the present invention may be implemented, and will then describe individual aspects of the present invention in detail.

A. General Description of an Ultrasonic Echographic System (FIG. 1)

The present invention is directed to a method and system for contrast agent detection and measurement using quadrature demodulation and the resulting information contained in the complex phasors, that is, magnitude and phase, of two or more successive return signals and the following presents three embodiments of the present invention. The following also compares the results obtained through the present invention with the results obtained through the magnitude only methods preferred in the prior art, hereafter referred to as the "difference of magnitudes" method.

As described above, the first returned signal is the vector sum of a phasor component due to the bubbles being destroyed by the insonication and other phasor components from other sources, such as the tissue, clutter and bubbles that were not destroyed by the insonication. The second returned signal, in turn, includes phasor components from the other sources, such as the tissue, clutter and bubbles that were not destroyed, but does not have a phasor component from the bubbles being destroyed by the insonication that generated the first returned signal, and the presence of a contrast agent is detected and measured by comparison of the complex phase information from the first and second return signals.

The first method described below, which will be referred to as the "magnitude of difference" method, determines the magnitude of the complex difference of the first and second return signals wherein both the magnitude components and the phase components of the complex return signals, in real and imaginary form, are used to determine the magnitude of the complex difference between the signals. The second method described below, which will be referred to as the "asymmetrical weighting" method resolves the complex difference into components in phase with and orthogonal to the second signal, and weights those two components differently for thresholding and/or magnitude calculation. The third method described below, which will be referred to as the "extrapolation" method uses three successive return signals along each receiving line wherein the second and third return signals are used to extrapolate what the first return signal would have been without the bursting bubble component and to generate a decision threshold that is compared to the complex difference between the actual first return signal and the extrapolated first return signal.

Referring to FIG. 1, therein is presented a diagrammatic block diagram of an ultrasonic echographic System 10 in which the present invention is implemented. It will be appreciated by those of ordinary skill in the relevant arts that System 10 as illustrated in FIG. 1, and the operation thereof as described herein below, is intended to be generally representative of such systems and that any particular system may differ from that shown in FIG. 1 in the details of the construction and operation of such as system. As such, the System 10 represented in FIG. 1 is to be regarded as illustrative and exemplary and not as limiting as regards the invention described herein or its implementations and embodiments or the claims hereto. It will also be noted that reference numerals 12 through 46 are not used in the following descriptions.

As illustrated in FIG. 1, and as is well known and understood in the relevant arts, a typical System 10, such as a Hewlett-Packard Sonos-2000, includes a Transducer 48 for transmitting lines, that is, beams or scan lines, of ultrasonic energy into a body and receiving the ultrasonic energy reflected from the internal structures of the body, including energy at the fundamental and second harmonic frequencies of a contrast agent present in the path of the current line or beam. A Transducer 48 is generally comprised of an array of piezoelectric elements that may be used individually or in combinations to form and steer the transmitting and receiving lines of Transducer 48. As is also well understood in the relevant art, the formation of transmitting lines by a Transducer 48 is accomplished by the selection of individual elements thereof to comprise an aperture for each transmitting or receiving line and the driving of the selected elements by signals having selected phase relationships. Receiving lines are formed in the same manner, except that the received "signal" is comprised of a received signal from each of the selected elements and the phase relationships of the individual received signals are controlled to form a single received signal forming the received line.

As illustrated in FIG. 1, a Transmitter and Receiver 50 drives Transducer 48 to transmit ultrasonic energy into a body being scanned, that is, to insonicate the tissues of interest and possibly containing a contrast agent. The returning signals are received from Transducer 48 by Transmitter and Receive 50 and are provided to Beamformer 52, which forms a single Return Signal 54 representing an image along a single receiving line, or scan line, of Transducer 48 wherein Return signal 54 is a real RF signal having magnitude and phase but is not complex.

Return Signal 54 is provided to an In Phase/Quadrature (I.Q.) Demodulator and Filter circuit 56 which demodulates and filters each Return Signal 54 to determine the in phase and quadrature components of each Return Signal 54, indicated as InPhase 58 and Quadrature 60, of each Return Signal 54. As is well understood by those of ordinary skill in the relevant arts, the in phase and quadrature components of a Return Signal 54 are the resolved complex components, real and imaginary, of the Return Signal 54 that are in phase with and in quadrature or orthogonal phase with a reference signal, wherein the reference signal may be the demodulating signal. As is well understood, the demodulated in phase and quadrature components of a Return Signal 54 are a function of, and thereby represent and are determined by, the magnitude and the phase of the return Signal 54.

The InPhase 58 and Quadrature 60 components of each Return Signal 54 are then provided to Contrast Agent Detector 62 which, as described below, determines the complex difference between a first Return Signal 54 and a subsequent Return Signal 54, which may be the next, or second, Return Signal 54 or any subsequent Return Signal 54, to generate a Complex Difference 64.

The Complex Difference 64 is then transformed into a magnitude representation that is then provided to a Scan Converter (Scan Convert) 66 that converts the Complex Difference 64 magnitude information into a form suitable for display, whereupon it is or may be combined with B Mode scan information in Combine W/B Mode 68 and displayed through a Display 70. Complex Difference 64 may also be used in the asymmetrical weighting method described in a following discussion. It will be understood that System 10 may generate other displays and perform yet other functions to display ultrasonic images. For example, the image data provided to Display 70 may processed further, for example, to enhance the images or to form three dimensional arrays of the data from the images received along the individual receiving lines to generate still further images, such as different cross sectional views of the cardiac structure. System 10 may be used to determine and display doppler information images representing, for example, the rates and patterns of blood flow in the heart chambers, and portions of an image or a set of images may be selected and enlarged for display, thereby providing a more detailed display of selected regions of interest.

B. Detailed Description of Preferred Embodiments

Figure 2C:
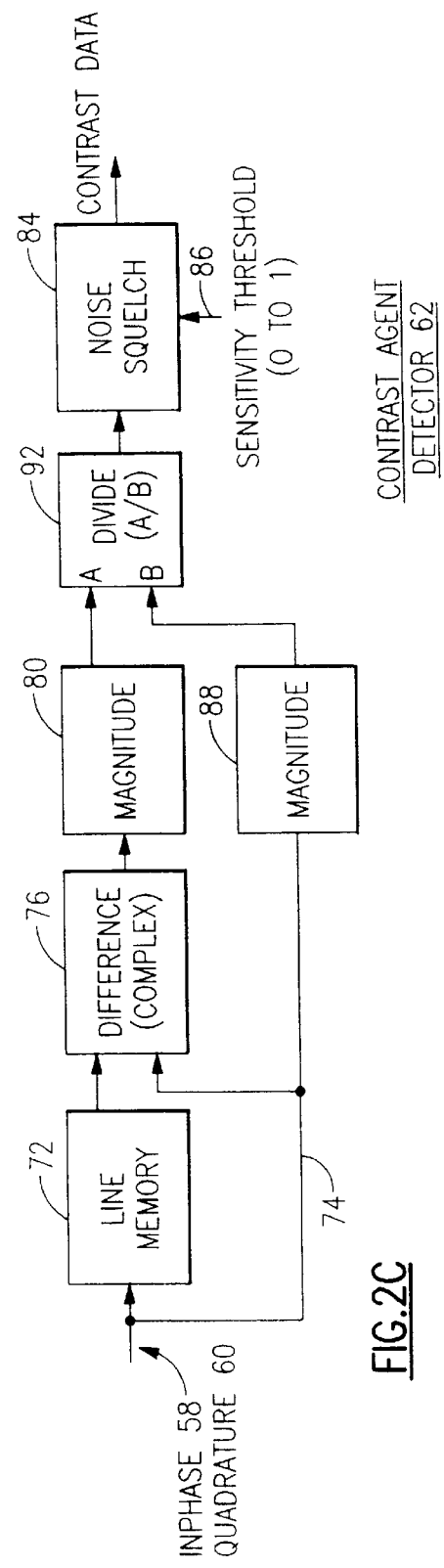

1. The Magnitude of Difference Method (FIGS. 2A, 2B, and 2C)

As described above, the magnitude of difference method determines the magnitude of the complex difference of successive pairs of a first return signal and a second return signal wherein both the real and imaginary components, which includes both magnitude and phase information, of the complex return signals are used to determine the magnitude of the complex difference between the signals.

It will be noted that in this method, as in any of the following implementations using any of the other methods of the present invention, the second return signal of a pair of return signals may, or may not, be used as the first return signal of the next pair of return signals, and so on, depending upon the desired result. For example, averaging detection results from the same direction, that is, along the same line, will give a more consistent result but a lower frame rate.

Referring now to FIG. 2A, therein is shown a block diagram of Contrast Agent Detector 62. As shown therein, Contrast Agent Detector 62 includes a Line Memory 72 for receiving and storing the InPhase 58 and Quadrature 60 components of a first Return Signal 54 until a second Return Signal 54 is received, wherein the second Return Signal 54 may be any selected subsequent Return Signal 54. As shown, Line Memory 72 is provided with a Bypass 74, so that the InPhase 58 and Quadrature 60 components of the second Return Signal 54 may be provided to Complex Difference logic 76 concurrently with the stored first Return Signal 54. It will also be noted that the second Return Signal 54 may also be stored in Line Memory 72, to become the first Return Signal 54 of the next successive pair of Return Signals 54, and so on, as discussed previously.

Complex Difference 76 then determines the difference between the InPhase 58 and Quadrature 60 components of the two Return Signals 54 of a current pair of Return Signals 54 to generate Complex Difference Data 78 wherein Complex Difference Data 78 will again have an in phase component and a quadrature component which are a function of and represent the complex difference between of the first and second Return Signals 54, that is, between the real and imaginary components. It should be noted, in this regard, that the complex difference will typically be performed in rectangular components rather than in polar coordinates but, in different implementations, could be performed in polar coordinates.

Complex Difference Data 78 is provided to Magnitude 80, which resolves the in phase and quadrature components of the Complex Difference Data 78 for each pair of first and second Return Signals 54 and provides Difference Magnitude Data 82 to Noise Squelch/Threshold 84 wherein Difference Magnitude Data 82 is a value representing the magnitude of the complex difference between the pair of first and second Return Signals 54, that is, the real and imaginary components. Noise Squelch/Threshold 84, in turn, suppresses noise in the data and compares the value of each Difference Magnitude Data 82, which represents the magnitude of the complex difference between the pair of first and second Return Signals 54, with a predetermined, selectable Threshold 86 value.

If the value of the Difference Magnitude Data 82 exceeds the Threshold 86 value, then the first Return Signal 54 is determined to have a bursting bubble component sufficiently large to indicate the present of a contrast agent and, if the value of the Difference Magnitude Data 82 is less than the Threshold 86 value, then the first Return Signal 54 is determined not to include a bursting bubble component and no contrast agent is indicated. In this regard, the output of Nose Squelch/Threshold 84 may be a Boolean value, that is, one bit indicating "yes/no", or may, for example, be the contrast magnitude or a function of the contrast magnitude, such as a value representing the logarithm of the contrast magnitude.

It has been discussed previously that the detection of a contrast agent in a region of interest in tissue requires separating the difference between first and second return signals due to the disappearance of contrast agent bubbles from changes in the return signal from the tissue itself As also discussed, however, the return signal component from the tissue can itself vary from return signal to return signal, for example, due to movement of the tissue or the transducer, changes in the tissue characteristics due to variations in blood perfusion, speckling, and other causes and sources other than the absence of bursting bubbles of contrast agent.

FIGS. 2B and 2C are accordingly block diagrams of implementations of the Contrast Agent Detector 62 of FIG. 2A wherein the value of Threshold 86 is proportional to the magnitude of the second Return Signal 54 which, as described, includes components from all sources except bursting bubbles. The embodiments of Contrast Agent Detectors 62 illustrated in FIGS. 2C and 2D therefore determine the value of Threshold 86 dependent upon the magnitude of the current second Return Signal 54, thereby adjusting the value of Threshold 86 according to the assumption that the magnitude of the tissue echo change is proportional to the magnitude of the tissue echo, that is, the magnitude of the echo due to the tissue.

Referring first to FIG. 2B, the Contrast Agent Detector 62 illustrated therein is similar to the Contrast Agent Detector 62 of FIG. 2A except that an additional Magnitude 88 circuit is connected from Bypass 74 to receive the InPhase 58 and Quadrature 60 components of the current second Return Signal 54 and to determine a Second Magnitude 90 representing the magnitude of the current second Return Signal 54, including both contributions from the tissue and from other causes and sources other than the bursting bubbles of contrast agent, such as blood or noise. The value of Second Magnitude 90 is then multiplied by a Multiply 92 circuit to generate the value of Threshold 86, which thereby more closely represents a threshold based upon the local signal magnitude from sources other than the burst bubbles.

Referring now to FIG. 2C, the embodiment of Contrast Agent Detector 62 shown therein is similar to that of FIG. 2B except that rather than adjusting the Threshold 86 value according to the magnitude of the current second Return Signal 54, the implementation shown in FIG. 2C adjusts the value of Difference Magnitude 82 proportional to the magnitude of the current second Return Signal 54. As shown in FIG. 2C, Difference Magnitude 82 from Magnitude 80 and Second Magnitude 90 from Magnitude 88 are provided as inputs to Divide 92, which divides the value of Difference Magnitude 82 by the value of Second Magnitude 90 with the result being provided to Noise Squelch/Threshold 84, as a selectable, fixed Threshold 86 as in the implementation of Contrast Agent Detector 62 illustrated in FIG. 2A. The implementation of Contrast Agent Detector 62 thereby effectively scales a quantity, that is, Difference Magnitude 82, relative to a selectable fixed Threshold 86, which is equivalent to the use of a variable Threshold 86 in the Contrast Agent Detector 62 illustrated in FIG. 2C.

Again, it will be noted with regard to the implementations of the present invention described with reference to Figs, 2B and 2C that the current second Return Signals 54 may be stored in Line Memory 72 to become the first Return Signal 54 of the next pair of first and second Return Signals 54, as discussed previously.

Figure 3:
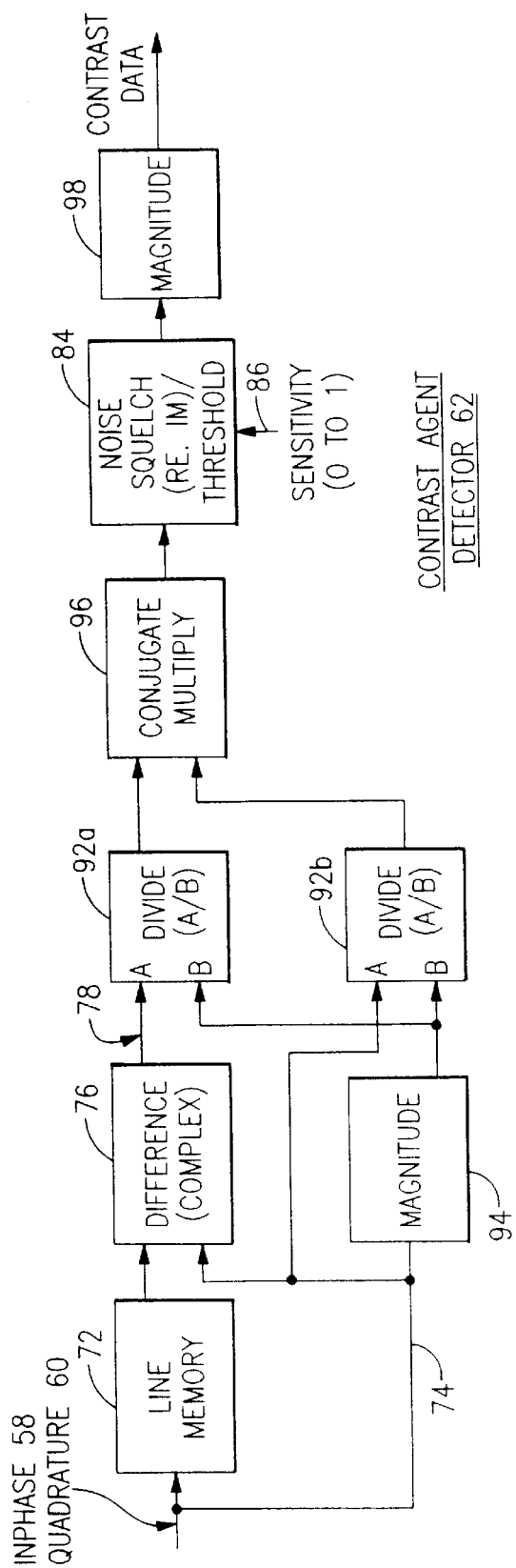
FIG. 3 is a block diagram of a contrast agent detector of the present invention implementing the asymmetrical weighting method of detection.

2. The Asymmetrical Weighting Method (FIG. 3)

As described briefly above, the "asymmetrical weighting" method resolves the complex difference between first and second return signals into components in phase with and orthogonal to the second signal, and weights these two components differently for thresholding and/or magnitude calculation.

The asymmetrical weighting method is based upon the principle that, as the change in the tissue component of the return signals between the first and second return signals is known to be primarily a phase rotation of the tissue component, the threshold for detecting the contrast agent bursting bubble component is more optimally an ellipse rather than a circle in the complex plane, where a threshold that appears as a circle in the complex plane is not a function of the phase angle component while a threshold that appears as an ellipse in the complex plane is a function of the phase angle component.

However, there are many ways to approximate an ellipse which may be simpler to implement in certain embodiments of the present method, such as a rectangle or rhombus. In the present implementation, regardless of the exact shape of the asymmetrical threshold, the complex difference between the first and second return signals is resolved into a component along the phase of the second return signal and a component orthogonal to the phase of the second return signal. The two components are then weighted differently in the thresholding operation and/or the magnitude calculation.

For an elliptical threshold, the two components are separately squared and added with different weighting coefficients and this sum is compared to a threshold which may or may not be dependent upon the magnitude of one of the signals. This sum of differently weighted squares may also be used for further processing, for example, to generate a color-coded display of the logarithm of the sum.

For a rhomboidal threshold, the magnitudes of the two components are added with different weighting coefficients and this sum is compared to a threshold which again may or may not be dependent upon the magnitude of one of the signals. This sum of differently weighted magnitudes may also be used for further processing, such as, and again, the generation of a color-coded display of the sum.

For a rectangular threshold, the greater of the differently weighted magnitudes of the two components is chosen and compared to a threshold which, again, may or may not be dependent on the magnitude of one of the signals. This maximum of differently weighted magnitudes may again also be used for further processing such as the generation of a color-coded display of the logarithm of the maximum of differently weighted magnitudes. A rectangular threshold may also be implemented by comparing the magnitudes of the two components to different thresholds and logically ORing the results of the comparison.

Finally, there are many other asymmetrical weighting, offsetting and combining methods which will be understood by those of ordinary skill in the relevant arts for generating other threshold shapes in the complex plane that approximate an ellipse in some way, such as a "football" threshold defined by portions of two circular arcs, a hexagon, and so on.

Referring now to FIG. 3, therein is illustrated a block diagram of an embodiment of Contrast Agent Detector 62 for the asymmetrical weighting method. As illustrated therein, the first Return Signal 54 is received and stored in a Line Memory 72 and provided to Complex Difference 76 together with a second Return Signal 54, which is routed through Bypass 74, to generate corresponding Complex Difference Data 78. Complex Difference Data 78 will have a real component which represents the difference between the real components of the first and second Return Signals 54, and an imaginary component which represents the difference between the imaginary components of the first and second Return Signals 54.

Complex Difference Data 78, in turn, is provided to an input of a Divide 92A. Divide 92A then divides the real and imaginary components of Complex Difference Data 78 by the magnitude of the second Return Signal 54 as provided from Magnitude 94, thereby scaling the magnitude of the complex difference data relative to a selectable fixed threshold, analogous to the technique discussed with regard to FIG. 2D, which is equivalent to the use of a variable signal-dependent threshold.

The second Return Signal 54 is also routed to a Magnitude 94, which determines the magnitude of the second Return Signal 54, and the original second Return Signal 54 together with the output of Magnitude 94 are provided as inputs to a Divide 92B. Divide 92B, in turn, divides the second Return Signal 54 by the magnitude of the second Return Signal 54, thereby providing an output representing the real and imaginary components of a unit-magnitude signal having the same phase as the second Return Signal 54.

The outputs of Divide 92A and Divide 92B are provided to Conjugate Multiply 96, which multiplies the scaled complex difference between the first and second Return Signals 54 by the conjugate of the unit-signal magnitude signal having the same phase as the second Return Signal 54. This operation effectively rotates the scaled complex difference in the complex plane, subtracting the phase angle of the second Return Signal 54. Conjugate Multiply 96 thereby generates an output wherein the real component represents the component of the scaled complex difference that is in phase with the second Return Signal 54, and the imaginary component represents the component of the scaled complex difference that is orthogonal to the second Return Signal 54.

The combined operation of Magnitude 94, Divide 92A, Divide 92B and Conjugate Multiply 96 implements a full complex division of Complex Difference Data 78 by second the Return Signal 54. It will be understood by those of ordinary skill in the arts, however, that the divide, multiply and magnitude calculations in the implementation described just above may be approximated by "short cut" methods that are familiar to those of ordinary skill in the relevant arts.

The complex output of Conjugate Multiply 96 is provided to Asymmetric Weighted Combiner 98 which weights the real and imaginary components with different coefficients and then combines them to form a magnitude-like positive number. Various possible combination methods have been described above, such as sum of differently weighted squares for an elliptical threshold, the sum of differently weighted magnitudes for a rhomboidal threshold, and maximum of differently weighted magnitudes for a rectangular threshold, and the implementation of these combination methods will be well understood by those of ordinary skill in the relevant arts.

The real positive output of Asymmetrical Weighted Combiner 98 is then provided to Noise Squelch/Threshold 84 which performs the same function as previously discussed, that is, values which fall below a threshold are set to zero, indicating no contrast agent detected, and values above the threshold indicate some contrast agent detected. Again, the output of Noise Squelch/Threshold 84 may be used as discussed previously to generate displays other than a Boolean "yes/no" result.

3. The Extrapolation Method (FIGS. 4A and 4B)

As summarized above, the extrapolation method uses three successive return signals along each receiving line wherein the second and third return signals are used to extrapolate what the first return signal would have been without the bursting bubble component and to generate a decision threshold that is compared to the complex difference between the actual first return signal and the extrapolated first return signal.

The extrapolation method is based upon the experimentally verified principle that the return signal component due to tissues are well correlated over several return signals. Accordingly, the System 46 implemented for the extrapolation method transmits three or more pulses along each transmitting/receiving line of the transducer and uses the second and third return signals, for example, to extrapolate what the first return signal would have been without the return signal component due to destroyed contrast agent. The extrapolation method then determines the complex difference between the actual first return signal and the extrapolated first return signal and the magnitude of the complex difference is compared to a threshold to determine the probability that a contrast agent is present in the tissues.

According to the extrapolation method, the threshold for detection needs only to be greater than the extrapolation error, instead of greater than the change in the return signal component due to the tissue itself In addition, the extrapolation error appears to be more symmetrical than the changes in the return signals due to the tissue component, so that asymmetrical weighting, as described above, may not be necessary. The combination of the extrapolation method with the asymmetrical weighting method may, however, be advantageous in at least certain circumstances and the implementation of the combination of the two methods will be apparent to those of ordinary skill in the relevant arts.

Still further in this regard, it will be noted that the changes in return signal components due to sources and causes other than the contrast agent primarily appear as a phase rotation. As such, the extrapolation method may advantageously be implemented and performed in polar coordinate representation of the data operated upon, that is, as magnitude and phase components, rather than in a rectangular coordinate representation of real and imaginary components of the signals. Rectangular coordinate representation, however, is more easily dealt with computationally and is adequate in instances wherein the tissue or transducer movements are relatively slow. As such, the following embodiment of the extrapolation method is described for a rectangular coordinate computation system, while the conversion of the embodiment shown herein to a polar coordinate computation system will be well understood by those of ordinary skill in the relevant arts.

Finally, it will be noted that the extrapolation method requires three receive signals per scan line rather than the two of the previously discussed methods. This is generally not a problem, however. For example, successive triplets of lines may be imaged in different directions and the pairs or triplets of lines in each direction could be interleaved with line pairs/triplets in other directions, as presently done in slow PRF color flow imaging.

In this regard, recent information regarding the destruction times and re-perfusion times of the contrast agent bubbles affects and helps determine how the ultrasonic scan lines should most be most optimally "fired" in the extrapolation method and this information may also be applied in the methods discussed previously.

First, it has been found that after the ultrasonic wave ruptures a bubble shell, the released gas requires some period of time, typically a few milliseconds, to dissolve into the blood. Since ultrasound lines are typically a few hundred microseconds in duration, successive lines close together in time will record the approximately exponential decay of the bubble echo as the gas dissolves, rather than the abrupt disappearance of the bubble echo from the first to the second line, as was originally assumed. In this regard, it should be noted that there exist certain special contrast agents, referred to as Cavisomes, that can also generate a strong return or sound from the bubble shell destruction and that appears only on the first echo line, although the gas still decays over milliseconds. This, within a group of successive ultrasound lines aimed in a particular direction, the lines are most optimally spaced a few milliseconds or tens of milliseconds apart in time. Lines aimed in other directions can be interleaved with the lines in one direction, however, so that the time is not wasted, and the lines rearranged, by manipulation in memory and addressing, before the detection process. This scan line interleaving process is well known in the art for color mapping slow velocity blood flow or tissue movement, and the data rearrangement is no more difficult than that performed in processing successive echos at different depths.

In addition, after most of the bubbles are destroyed by ultrasound pulses, new bubbles from elsewhere in the circulatory system require some period of time to flow into the volume being examined. In the case of capillary networks, this time is referred to as the re-perfusion interval and typically requires about one second. Since an entire frame of ultrasound data can be acquired in less than 100 milliseconds, even with several lines in each direction, there must be a pause between frames to allow for re-perfusion. For cardiac imaging such a slow frame rate cannot show the entire heart cycle, so that the frames must be triggered to always occur at the same point in the heart cycle to maintain a steady image. It has been found empirically that a frame every other heart cycle, roughly a frame every two seconds, is the optimum tradeoff between frame rate and reperfusion.

In general, therefore, the number of lines in each direction used for bubble detection there does not affect the frame rate in a significant manner since the frames are acquired only intermittently to allow reperfusion. The extrapolation method that uses three lines instead of the two lines used in the other methods described herein could therefore be extended to more than three lines to form an even more robust estimate of what the initial echo would have been without the bubbles that burst. It is still desirable that the frame acquisition time be reasonable short, however, so that the heart does not move too much during a frame, so that the use of interleaving as described just above is advantageous while the use of four or even five lines in each direction would most probably provide a sufficiently short frame acquisition time, and the apparatus and method of the extrapolation method as described herein may be modified accordingly.

Referring now to FIG. 4A, it is shown therein that the Contrast Agent Detector 62 implemented therein for the extrapolation method includes two Line Memories 72, designated as Line Memory 72a and Line Memory 72b, with a Bypass 74. Line Memories 72a and 72b respectively receive and store the first and second received Return Signals 54 while the currently received Return Signal 54 passes around Line Memories 72a and 72b to be provided to Complex Sum 100 as a third Received Signal 54 in parallel with the current second and first Received Signals 54 which are provided, respectively, from the outputs of Line Memory 72b and 72a. In addition, and as shown in FIG. 4A, the current second Return Signal 54 is provided from Line Memory 72b to a Magnitude 102.

Complex Sum 100 performs a complex phasor summation of the current first, second and third Return Signals 54 to generate a result that represents the difference between the actual current first Return Signal 54, as provided from Line Memory 72a, and an extrapolation, generated from the current second and third Return Signal 54 outputs provided from Line Memory 72b and Bypass 74, of what the current first Return Signal 54 would be without a contribution from a contrast agent. As indicated in FIG. 4A, this is accomplished in a summation wherein the first and third Return Signals 54 are summed with multipliers of +1 and the second Return Signal 54 is summed with a −2 multiplier.

The result is thereby a complex phasor representing summation of the first return signal, which includes contributions from the tissue, a contrast agent, if any, and other sources, plus the third return signal, which includes contributions from the tissue and other sources, thereby representing a sum including a contribution from the contrast agent, if any, plus two contributions from the tissue and other sources, minus twice the second return signal, which thereby includes two contributions from the tissue and other sources. The output of Complex Sum 100 thereby represents the difference between the current first Return Signal 54 and the extrapolation from the current second and third Return Signals 54 wherein the contributions from the tissue and other sources from the first, second and third return signals will usually nearly cancel, so that the resulting sum output of Complex Sum 100 primarily represents the contribution from the contrast agent, if any. Therefore, not only does the tissue contribution nearly cancel, but the change in tissue contribution between successive signals also nearly cancels. Complex Sum 100 thereby performs a signal processing operation referred to as a 2-zero filter, otherwise referred to mathematically as a second difference.

The output of Complex Sum 100 is then passed to Magnitude 104, which determines the magnitude of the complex sum.

At the same time as the above operations, the second Return Signal 54 is operated upon by Magnitude 102, which determines the magnitude of the second Return Signal 54 and passes the result to Multiply 106, which multiplies the magnitude of the second Return Signal 54 to generate a value representing a Threshold 86 as a proportion of the magnitude of the second Return Signal 54. Threshold 86 and the output of Magnitude 104 are provided to Noise Squelch/Threshold 84, which determines whether the difference between the actual current first Return Signal 54 and an extrapolation, generated from the current second and third Return Signals 54, of what the current first Return Signal 54 would be without a contribution from a contrast agent exceed the Threshold 86, which is a function of the magnitude of the current second Return Signal 54 and generates an output accordingly.

Referring now to FIG. 4B, therein is shown an alternate embodiment of the Contrast Agent Detector 62 incorporating the extrapolation method. As illustrated therein, the extrapolation method Contrast Agent Detector 62 of FIG. 4C is generally similar in structure and operation to that illustrated in FIG. 4A except that Line Memories 72a and 72b are arranged sequentially and Complex Sum 100 is replaced by Complex Differences 108a and 108b which are in sequence with Line Memories 72a and 72b. As a result, the single stage computation of the difference between the actual current first Return Signal 54 and an extrapolation, generated from the current second and third Return Signals 54, of what the current first Return Signal 54 would be without a contribution from a contrast agent by Complex Sum 100 is replaced by a multi-stage computation of the same factor by Complex Differences 108a and 108b.

That is, Line Memory 72b receives and stores a first Return Signal 54 of a series of three Return Signals 54 and the stored first Return Signal 54 and the next received Return Signal 54, that is, the second Return Signal 54, are provided to Complex Difference 108a, which determines the complex difference between the first and second Return Signals 54. The second Return Signal 54 is stored in Line Memory 72b, while the difference between the first and second Return Signals 54 is stored in Line Memory 72a.

During the next Return Signal 54 period, the next Return Signal 54, that is, the third Return Signal 54 is received and stored in Line Memory 72b, in the manner described above, and is provided through Bypass 74 to Complex Difference 108a together with the second Return Signal 54, which as stored in Line Memory 72b and is now provided therefrom to Complex Difference 108a.

Complex Difference 108a determines the complex difference between the second and third Return Signals 54 and provides the complex difference between the second and third Return Signals 54 to Line Memory 72a, to be stored therein, and through a Bypass 110 to an input of Complex Difference 108b. At the same time, the previously determined complex difference between the first and second Return Signals 54, which had previously been stored in Line Memory 72a, is read from Line Memory 72a and provided to the other input of Complex Difference 108b.

Complex Difference 108b then determines the complex difference between the complex difference between the second and third Return Signals 54 and the complex difference between the first and second Return Signals 54, so that the output of Complex Difference 108b is again the complex difference between the actual current first Return Signal 54 and an extrapolation, generated from the current second and third Return Signals 54, of what the current first Return Signal 54 would be without a contribution from a contrast agent.

The above process continues for successive groups of three successive Return Signals 54, in the manner described with respect to FIG. 4A, and with successive second Return Signals 54 being provided to Magnitude 102 in correspondence with the outputs of Complex Difference 108b to generate successive Thresholds 86.

4. Comparisons of Methods (FIGS. 5A through 5I)

The results of simulations indicating false negative and false positive results as a function of tissue echo power over the range of −40 db to +40 db and relative to a fixed contrast agent echo power for systems employing the difference of magnitudes method of the prior art and the magnitude of differences, asymmetrical weighting and extrapolation methods of the present invention are shown in FIGS. 5A through 5H.

Figure 5A:
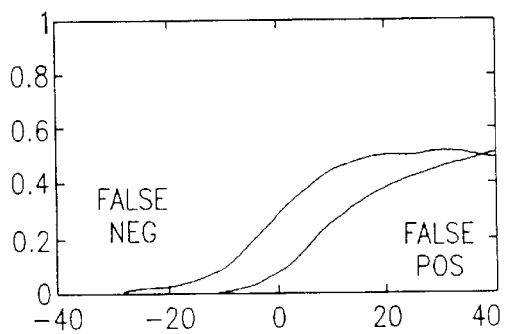
Figure 5B:
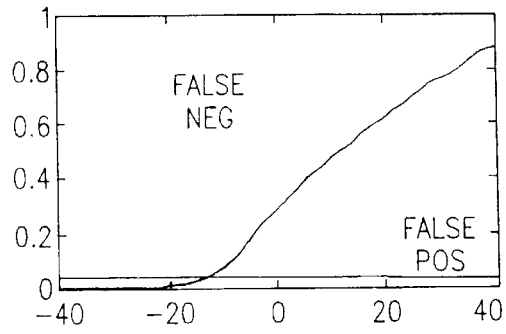

FIGS. 5A and 5B represent the test results for the difference of magnitudes, that is, phase independent, method of the prior art for, respectively fixed and variable thresholds.

Figure 5C:
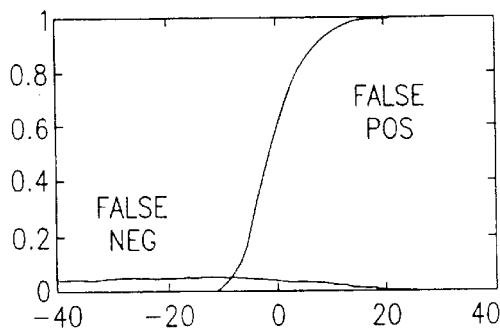
Figure 5D:
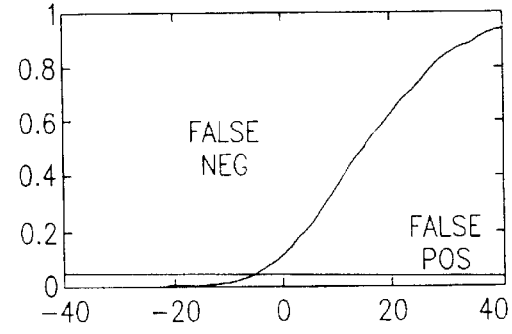

FIGS. 5C and 5D represent the test results for the magnitude of difference method of the present invention for, respectively, fixed and variable thresholds.

Figure 5E:
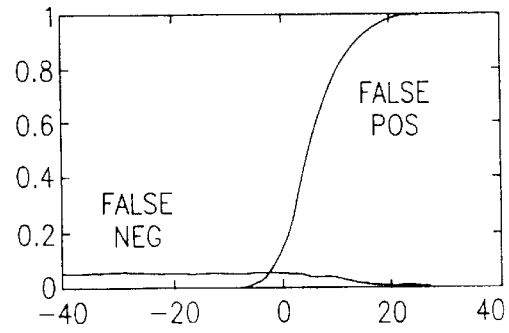
Figure 5F:
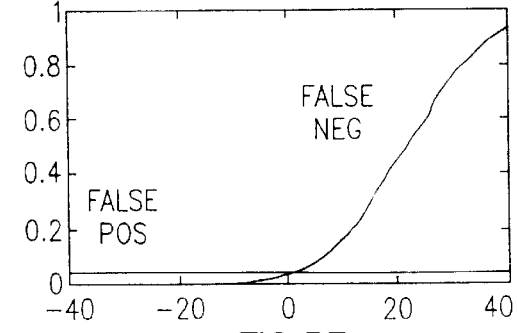
Figure 5G:
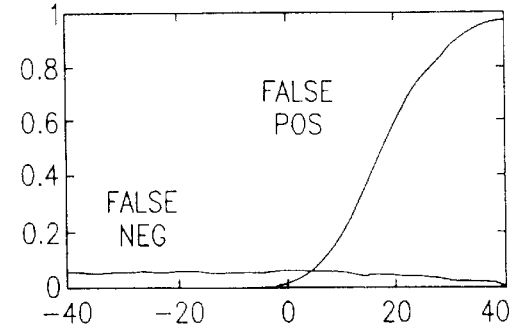
Figure 5H:
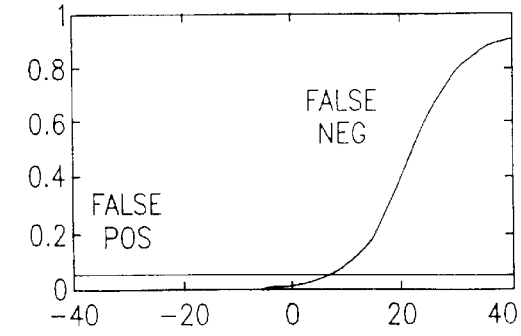

FIGS. 5E and 5F represent the test results for the asymmetrical weighting method of the present invention for, respectively, fixed and variable thresholds, and FIGS. 5G and 5H represent the test results for the extrapolation method of the present invention for, respectively, fixed and variable thresholds.

The results of these tests are further represented in FIG. 5I, which shows the tissue echo power level at which there resulted a 5% probability of either a false positive or a false negative result in the detection of a contrast agent. In FIG.

5I, Lines A and B correspond to the difference of magnitudes method of the prior art for fixed and variable thresholds, while, in a like manner, Lines C and D correspond to the magnitude of difference method of the present invention for fixed and variable thresholds, Lines E and F correspond to the asymmetrical weighting method of the present invention for fixed and variable thresholds, and Lines G and H correspond to the extrapolation method of the present invention for fixed and variable thresholds.

It is apparent that a larger value of tissue echo power at which the false result level reaches 5% is preferable and it may be seen from FIG. 5I that the difference of magnitudes method of the prior art yielded the poorest result while the extrapolation method of the present invention yielded the most advantageous result.

It will also be seen from FIGS. 5A through 5H that fixed and variable thresholds tend to have opposite effects as regards the onset of error levels, with fixed thresholds tending to generate false positive results, that is, tending to error in detecting a contrast agent when no bubbles are present and variable thresholds tending to generate false negative results, that is, tending to error in indicating no bubbles when, in fact, a contrast agent is present. A system may therefore be implemented with both fixed and variable thresholds, with the user selecting the probability trend of errors depending upon personal preference and specific circumstances.

It will also be noted that the provision of two parameters in the asymmetrical weighting method of the present invention may be regarded as an advantage or a disadvantage, providing greater versatility but making use of the system more complex as regards finding optimum settings of the parameters.

Lastly, while the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims. Therefore, it is the object of the appended claims to cover all such variation and modifications of the invention as come within the true spirit and scope of the invention.

What is claimed is:

1. In an ultrasonic echographic system receiving return signals wherein each return signal represents an image along a single receiving line, a quadrature demodulation contrast agent detector, comprising:

an in phase/quadrature demodulator for determining the in phase and quadrature components of each return signal and providing resolved complex amplitude and phase components of each return signal, wherein
the in phase and quadrature components of each return signal are the resolved complex amplitude and phase components, real and imaginary, of each return signal that are respectively in phase with and in quadrature phase with a reference signal, and a contrast agent detector for determining the complex difference between the resolved complex amplitude and phase components of a first return signal and the resolved complex amplitude and phase components of a second return signal and generating a complex difference value representing the magnitude of a complex amplitude and phase difference between the resolved first and second signals due to a contrast agent.

2. The quadrature demodulation contrast agent detector of claim 1, wherein the contrast agent detector further comprises:

a magnitude of difference detector for determining the magnitude of the complex difference of pairs of a first return signal and a second return signal wherein both the real and imaginary components of the return signals, which include both magnitude and phase information, are used to determine the magnitude of the complex difference between the first and second return signals.

3. In an ultrasonic echographic system receiving return signals wherein each return signal represents an image along a single receiving line, a quadrature demodulation contrast agent detector, comprising:

an in phase/quadrature demodulator for determining the in phase and quadrature components of each return signal and providing resolved complex amplitude and phase components of each return signal, wherein
the in phase and quadrature components of each return signal are the resolved complex amplitude and phase components, real and imaginary, of each return signal that are respectively in phase with and in quadrature phase with a reference signal, and a contrast agent detector for determining the complex difference between the resolved complex amplitude and phase components of a first return signal and the resolved complex amplitude and phase components of a second return signal and generating a complex difference value representing the magnitude of a complex amplitude and phase difference between the resolved first and second signals due to a contrast agent, a magnitude of difference detector for determining the magnitude of the complex difference of pairs of a first return signal and a second return signal wherein both the real and imaginary components of the return signals, which include both magnitude and phase information, are used to determine the magnitude of the complex difference between the first and second return signals, a complex difference calculator for determining the difference between the in phase and quadrature components of the first and second return signals and generating a complex difference value for each pair of first and second return signals wherein each complex difference value will have an in phase component and a quadrature component representing the complex difference between the real and imaginary components of the first and second return signals, a magnitude resolver for resolving the in phase and quadrature components of the complex difference value for each pair of first and second return signals and generating a difference magnitude value representing the magnitude of the complex difference between the real and imaginary components of each pair of first and second return signals, and a threshold comparator for comparing the value of the difference magnitude value of each pair of first and second return signals with a predetermined, selectable threshold value and generating an output representing a contrast agent component when a difference magnitude value exceeds the threshold value.

4. The quadrature demodulation contrast agent detector of claim 3 wherein the magnitude of difference contrast agent detector comprises:

a memory for receiving and storing the in phase and quadrature components of the first return signal and providing the in phase and quadrature components of the first return signal to the complex difference calculator, and a bypass connected around the memory for providing the in phase and quadrature components of the second return signal to the complex difference calculator concurrently with the stored in phase and quadrature components of the first return signal.

5. The quadrature demodulation contrast agent detector of claim 3, wherein the contrast agent detector further comprises:

a second magnitude resolver for receiving the in phase and quadrature components of the second return signal and determining a second magnitude value representing the magnitude of the second return signal, including both contributions from the tissue and from other causes and sources other than the contrast agent, and a multiplier for receiving the second magnitude value and multiplying the second magnitude value by a predetermined value to generate a threshold value representing a proportion of the signal magnitude from sources other than the contrast agent.

6. The quadrature demodulation contrast agent detector of claim 3, wherein the contrast agent detector further comprises:

a second magnitude resolver for receiving the in phase and quadrature components of the second return signal and determining a second magnitude value representing the magnitude of the second return signal, including both contributions from the tissue and from other causes and sources other than the contrast agent, and a divider for receiving the difference magnitude value and the second magnitude value and dividing the value of the difference magnitude value by the value of the second magnitude value to generate the threshold value thereby scaling the difference magnitude value relative to a selectable fixed threshold value to provide a variable threshold value relative to the magnitude of the second return signal, including both contributions from the tissue and from other causes and sources other than the contrast agent.

7. In an ultrasonic echographic system receiving return signals wherein each return signal represents an image along a single receiving line, a quadrature demodulation contrast agent detector, comprising:

an in phase/quadrature demodulator for determining the in phase and quadrature components of each return signal and providing resolved complex amplitude and phase components of each return signal, wherein the in phase and quadrature components of each return signal are the resolved complex amplitude and phase components, real and imaginary, of each return signal that are respectively in phase with and in quadrature phase with a reference signal, and a contrast agent detector for determining the complex difference between the resolved complex amplitude and phase components of a first return signal and the resolved complex amplitude and phase components of a second return signal and generating a complex difference value representing the magnitude of a complex amplitude and phase difference between the resolved first and second signals due to a contrast agent, wherein the contrast agent detector includes an asymmetrical weighting detector for resolving the complex difference between first and second return signals into components in phase with and orthogonal to the second signal and weighting these two components differently for generating corresponding threshold values for the in phase and orthogonal components of the complex difference between the first and second return signals wherein a contrast agent is indicated when one of the in phase or orthogonal components exceeds the corresponding threshold value.

8. The quadrature demodulation contrast agent detector of claim 7, wherein the asymmetrical weighting detector further comprises:

a complex difference calculator for determining the difference between the in phase and quadrature components of the first and second return signals and generating a complex difference value for each pair of first and second return signals wherein each complex difference value has a real component value which represents the difference between the real components of the first and second return signals and an imaginary component value which represents the difference between the imaginary components of the first and second return signals, a magnitude resolver for receiving the second return signal and generating a value representing the magnitude of the second return signal, a first divider for receiving the complex difference value and dividing the real and imaginary component values by the value representing the magnitude of the second return signal and generating a scaled complex difference signal representing the complex difference between the first and second return signals, a second divider for receiving the second return signal and the value representing the magnitude of the second return signal and dividing the second return signal by the value representing the magnitude of the second return signal for generating a unit magnitude signal representing the real and imaginary components of the second return signal and in phase with the second return signal, a conjugate multiplier for receiving the outputs of the first and second dividers and multiplying the scaled complex difference signal by the conjugate of the unit magnitude signal generate a scaled complex difference signal rotated in the complex plane and having a real component representing the scaled complex difference in phase with the second return signal and an imaginary component orthogonal to the second return signal, an asymmetric weighted combiner for receiving the rotated scaled complex difference signal, weighting the real and imaginary components of the rotated scaled complex difference signal with corresponding coefficients, and combining the weighted real and imaginary components to generate a combined magnitude value, and a threshold comparator for comparing the combined magnitude value with a predetermined, selectable threshold value and generating an output representing a contrast agent component when a difference magnitude value exceeds the threshold value.

9. The quadrature demodulation contrast agent detector of claim 8 wherein the asymmetrical weighting detector further comprises:

a memory for receiving and storing the in phase and quadrature components of the first return signal and providing the in phase and quadrature components of the first return signal to the complex difference calculator, and a bypass connected around the memory for providing the in phase and quadrature components of the second return signal to the complex difference calculator, to the magnitude resolver and to the first divider concurrently with the stored in phase and quadrature components of the first return signal.

10. The quadrature demodulation contrast agent detector of claim 8 wherein the asymmetric weighted combiner weights the real and imaginary components of the rotated scaled complex difference signal by separately squaring and adding the real and imaginary components with different weighting coefficients so that the combined magnitude value that is compared to the threshold defines an elliptical threshold in the complex plane.

11. The quadrature demodulation contrast agent detector of claim 8 wherein the asymmetric weighted combiner weights the magnitudes of real and imaginary components of the rotated scaled complex difference signal by adding the real and imaginary components with corresponding weighting coefficients so that the combined magnitude value that is compared to the threshold defines a rhomboidal threshold in the complex plane.

12. The quadrature demodulation contrast agent detector of claim 8 wherein the asymmetric weighted combiner weights the real and imaginary components of the rotated scaled complex difference signal by separately weighting the real and imaginary magnitudes with corresponding coefficients and comparing the greater of the weighted real and imaginary magnitudes with the threshold so that the combined magnitude value that is compared to the threshold defines a rectangular threshold in the complex plane.

13. In an ultrasonic echographic system receiving return signals wherein each return signal represents an image along a single receiving line, a quadrature demodulation contrast agent detector, comprising:
   an in phase/quadrature demodulator for determining the in phase and quadrature components of each return signal and providing resolved complex amplitude and phase components of each return signal, wherein
      the in phase and quadrature components of each return signal are the resolved complex amplitude and phase components, real and imaginary, of each return signal that are respectively in phase with and in quadrature phase with a reference signal, and
   a contrast agent detector for determining the complex difference between the resolved complex amplitude and phase components of a first return signal and the resolved complex amplitude and phase components of a second return signal and generating a complex difference value representing the magnitude of a complex amplitude and phase difference between the resolved first and second signals due to a contrast agent, wherein the contrast agent detector includes
      an extrapolation detector for receiving three successive return signals along each receiving line wherein the second return signal and a third return signal are used to extrapolate what the first return signal would have been without the contrast agent component and to generate a decision threshold that is compared to the complex difference between the actual first return signal and the extrapolated first return signal.

14. The quadrature demodulation contrast agent detector of claim 13 wherein the extrapolation detector further comprises:
   a complex summer for receiving the first, second and third return signals and performing a complex phasor summation of the first, second and third return signals to generate a complex sum that represents the difference between the actual first return signal and an extrapolated first return signal generated from the second and third return signals and without a contribution from a contrast agent,
   a first magnitude resolver for receiving the complex and generating a value representing the magnitude of the complex sum,
   a second magnitude resolver for receiving the second return signal and generating a value representing the magnitude of the second return signal,
   a multiplier for receiving the value representing the magnitude of the second return signal and multiplying the value representing the magnitude of the second return signal by a coefficient to generate a threshold value, and
   a threshold comparator for receiving the threshold value and the complex sum representing the difference between the actual first return signal and the extrapolated first return signal and generating an output representing whether the complex sum exceeds the threshold value.

15. The quadrature demodulation contrast agent detector of claim 14 wherein the complex summer generates a complex sum of the first, second and third return signals wherein the first and third return signals are summed with multipliers of +1 and the second return signal is summed with a −2 multiplier.

16. The quadrature demodulation contrast agent detector of claim 14 wherein the extrapolation detector further comprises:
   a first memory and a second memory, each for receiving and storing the first, second and third return signals,
      the first memory providing the first return signal to the complex summer, and
      the second memory providing the second return signal to the complex summer and to the first magnitude resolver, and
   a bypass for providing the third return signal to the complex summer.

17. The quadrature demodulation contrast agent detector of claim 13 wherein the extrapolation detector further comprises:
   a first complex difference calculator for generating a first complex difference between the first and second return signals,
   a second complex difference calculator for generating a second complex difference representing the complex difference between the second and third return signals and the first complex difference, the second complex difference thereby representing the complex difference between the actual first return signal and an extrapolated first return signal generated from the second and third return signals and not including a contrast agent component,
   a magnitude resolver for receiving the second return signal and generating a value representing the magnitude of the second return signal,
   a multiplier for receiving the value representing the magnitude of the second return signal and multiplying the value representing the magnitude of the second return signal by a coefficient to generate a threshold value, and
   a threshold comparator for receiving the threshold value and the complex sum representing the difference between the actual first return signal and the extrapolated first return signal and generating an output representing whether the complex sum exceeds the threshold value.

18. The quadrature demodulation contrast agent detector of claim 17 wherein the extrapolation detector further comprises:
- a first memory for storing the first return signal, the second return signal and the third return signal and providing the first return signal to the first complex difference calculator,
- a first bypass for providing the second return signal to the first difference calculator in conjunction with the first return signal from the first memory and the second return signal to the magnitude resolver,
- a second memory for storing the first complex difference between the first and second return signals and the second complex difference representing the complex difference between the second and third return signals, and
- a second bypass for providing the second complex difference between the second return signal and the third return signal to the second complex difference calculator in conjunction with the first complex difference between the first return signal and the second return signal from the second memory.

19. In an ultrasonic echographic system receiving return signals wherein each return signal represents an image along a single receiving line, a quadrature demodulation contrast agent detector, comprising:
- an in phase/quadrature demodulator for determining the in phase and quadrature components of each return signal and providing resolved complex amplitude and phase components of each return signal, wherein
  - the in phase and quadrature components of each return signal are the resolved complex amplitude and phase components, real and imaginary of each return signal that are respectively in phase with and in quadrature phase with a reference signal, and
- a contrast agent detector for determining the complex difference between the resolved complex amplitude and phase components of a first return signal and the resolved complex amplitude and phase components of a second return signal and generating a complex difference value representing the magnitude of a complex amplitude and phase difference between the resolved first and second signals due to a contrast agent, wherein
  the contrast agent detector includes
  - an extrapolation detector for receiving a first return signal and n subsequent successive return signals along each receiving line wherein the n successive return signals are used to extrapolate what the first return signal would have been without the contrast agent component and to generate a decision threshold that is compared to the complex difference between the actual first return signal and the extrapolated first return signal.

20. The quadrature demodulation contrast agent detector of claim 19 wherein the extrapolation detector further comprises:
- a complex summer for receiving the first return signal and n subsequent successive return signals and performing a complex phasor summation of the first return signal and the n subsequent successive return signals to generate a complex sum that represents the difference between the actual first return signal and an extrapolated first return signal generated from the n subsequent successive return signals and without a contribution from a contrast agent,
- a first magnitude resolver for receiving the complex sum and generating a value representing the magnitude of the complex sum,
- a second magnitude resolver for receiving the n subsequent successive return signals and generating a value representing the magnitude of the n subsequent successive return signals,
- a multiplier for receiving the value representing the magnitude of the n subsequent successive return signals and multiplying the value representing the magnitude of the n subsequent successive return signals by a coefficient to generate a threshold value, and
- a threshold comparator for receiving the threshold value and the complex sum representing the difference between the actual first return signal and the extrapolated first return signal and generating an output representing whether the complex sum exceeds the threshold value.

21. The quadrature demodulation contrast agent detector of claim 20 wherein the first and n subsequent successive return signals in a given direction are interleaved with a first and n subsequent successive return signals in at least one other given direction and an extrapolated first return signal is generated for each given direction.

22. In an ultrasonic echographic system receiving return signals wherein each return signal represents an image along a single receiving line, a method for quadrature demodulation detection of a contrast agent, comprising the steps of:
- determining the in phase and quadrature components of each return signal and providing resolved complex amplitude and phase components of each return signal, wherein
  the in phase and quadrature components of each return signal are the resolved complex amplitude and phase components, real and imaginary, of each return signal that are respectively in phase with and in quadrature phase with a reference signal, and
- detecting a contrast agent by determining the complex difference between the resolved complex amplitude and phase components of a first return signal and the resolved complex amplitude and phase components of a second return signal, and
- generating a complex difference value representing the magnitude of a complex amplitude and phase difference between the resolved first and second signals due to a contrast agent.

23. The method for quadrature demodulation detection of a contrast agent of claim 22, wherein the step of detecting a contrast agent detector further comprises the step of:
- determining the magnitude of the complex difference of pairs of a first return signal and a second return signal wherein both the real and imaginary components of the return signals, which include both magnitude and phase information, are used to determine the magnitude of the complex difference between the first and second return signals.

24. In an ultrasonic echographic system receiving return signals wherein each return signal represents an image along a single receiving line, a method for quadrature demodulation detection of a contrast agent, comprising the steps of:
- determining the in phase and quadrature components of each return signal and providing resolved complex amplitude and phase components of each return signal, wherein
  the in phase and quadrature components of each return signal are the resolved complex amplitude and phase components real and imaginary of each return signal that are respectively in phase with and in quadrature phase with a reference signal, and detecting a contrast agent by determining the complex difference between the resolved complex amplitude and phase components of a first return signal and the resolved complex amplitude and phase components of a second return signal, and generating a complex difference value representing the magnitude of a complex amplitude and phase difference between the resolved first and second signals due to a contrast gent.

determining the difference between the in phase and quadrature components of the first and second return signals and generating a complex difference value for each pair of first and second return signals wherein each complex difference value will have an in phase component and a quadrature component representing the complex difference between the real and imaginary components of the first and second return signals, resolving the in phase and quadrature components of the complex difference value for each pair of first and second return signals and generating a difference magnitude value representing the magnitude of the complex difference between the real and imaginary components of each pair of first and second return signals, and comparing the value of the difference magnitude value of each pair of first and second return signals with a predetermined, selectable threshold value and generating an output representing a contrast agent component when a difference magnitude value exceeds the threshold value.

25. The method for quadrature demodulation detection of a contrast agent of claim 24 wherein the step of detecting a contrast agent further comprises the steps of:

receiving and storing the in phase and quadrature components of the first return signal and providing as an output the in phase and quadrature components of the first return signal to the complex difference calculator from the memory, and providing the in phase and quadrature components of the second return signal and an output for determining the complex difference concurrently with the stored in phase and quadrature components of the first return signal through bypass connected around the memory.

26. The method for quadrature demodulation detection of a contrast agent of claim 24 wherein the step of detecting a contrast agent further comprises the steps of:

from the in phase and quadrature components of the second return signal, determining a second magnitude value representing the magnitude of the second return signal, including both contributions from the tissue and from other causes and sources other than the contrast agent, and multiplying the second magnitude value by a predetermined value to generate a threshold value representing the signal magnitude from sources other than the contrast agent.

27. The method for quadrature demodulation detection of a contrast agent of claim 24 wherein the step of detecting a contrast agent further comprises the steps of:

determining a second magnitude value representing the magnitude of the second return signal, including both contributions from the tissue and from other causes and sources other than the contrast agent, and dividing the value of the difference magnitude value by the value of the second magnitude value to generate the threshold value thereby scaling the difference magnitude value relative to a selectable fixed threshold value to provide a variable threshold value relative to the magnitude of the second return signal, including both contributions from the tissue and from other causes and sources other than the contrast agent.

28. In an ultrasonic echographic system receiving return signals wherein each return signal represents an image along a single receiving line, a method for quadrature demodulation detection of a contrast agent comprising the steps of:

determining the in phase and quadrature components of each return signal and providing resolved complex amplitude and phase components of each return signal, wherein the in phase and quadrature components of each return signal are the resolved complex amplitude and phase components, real and imaginary of each return signal that are respectively in phase with and in quadrature phase with a reference signal, and detecting a contrast agent by determining the complex difference between the resolved complex amplitude and phase components of a first return signal and the resolved complex amplitude and phase components of a second return signal, and generating a complex difference value representing the magnitude of a complex amplitude and phase difference between the resolved first and second signals due to a contrast agent resolving the complex difference between first and second return signals into components in phase with and orthogonal to the second signal, weighting the in phase and orthogonal components differently for generating corresponding threshold values for the in phase and orthogonal components of the complex difference between the first and second return signals, and indicating a contrast agent when an asymmetric combination of the magnitudes of the in phase or orthogonal components exceeds the corresponding threshold value.

29. The method for quadrature demodulation detection of a contrast agent of claim 28 wherein the step of detecting a contrast agent further comprises the steps of:

determining the difference between the in phase and quadrature components of the first and second return signals and generating a complex difference value for each pair of first and second return signals wherein each complex difference value has a real component value which represents the difference between the real components of the first and second return signals and an imaginary component value which represents the difference between the imaginary components of the first and second return signals, generating a value representing the magnitude of the second return signal, dividing the real and imaginary component values by the value representing the magnitude of the second return signal and generating a scaled complex difference signal representing the complex difference between the first and second return signals, dividing the second return signal by the value representing the magnitude of the second return signal for generating a unit magnitude signal representing the real and imaginary components of the second return signal and in phase with the second return signal, multiplying the scaled complex difference signal by the conjugate of the unit magnitude signal generate a scaled complex difference signal rotated in the complex plane and having a real component representing the scaled complex difference in phase with the second return signal and an imaginary component orthogonal to the second return signal, weighting the real and imaginary components of the rotated scaled complex difference signal with corresponding coefficients, and combining the weighted real and imaginary components to generate a combined magnitude value, and comparing the combined magnitude value with a predetermined, selectable threshold value and generating an output representing a contrast agent component when a difference magnitude value exceeds the threshold value.

30. The method for quadrature demodulation detection of a contrast agent of claim 29 wherein the step of detecting a contrast agent further comprises the steps of storing the in phase and quadrature components of the first return signal and providing as an output the in phase and quadrature components of the first return signal to the complex difference calculator, and providing the in phase and quadrature components of the second return signal as outputs for determining the difference between the in phase and quadrature components and for generating a scaled complex difference signal concurrently with the stored in phase and quadrature components of the first return signal.

31. The method for quadrature demodulation detection of a contrast agent of claim 29 wherein the step of weighting the real and imaginary components of the rotated scaled complex difference signal by the asymmetric weighted combiner further comprises the step of:

separately squaring and adding the real and imaginary components with different weighting coefficients so that the combined magnitude value that is compared to the threshold defines an elliptical threshold in the complex plane.

32. The method for quadrature demodulation detection of a contrast agent of claim 29 wherein the step of weighting the real and imaginary components of the rotated scaled complex difference signal by the asymmetric weighted combiner further comprises the step of:

adding magnitudes of the real and imaginary components with corresponding weighting coefficients so that the combined magnitude value that is compared to the threshold defines a rhomboidal threshold in the complex plane.

33. The method for quadrature demodulation detection of a contrast agent of claim 29 wherein the step of weighting the real and imaginary components of the rotated scaled complex difference signal by the asymmetric weighted combiner further comprises the step of:

separately weighting the magnitudes of the real and imaginary components with corresponding coefficients and comparing the greater of the weighted real and imaginary components with the threshold so that the combined magnitude value that is compared to the threshold defines a rectangular threshold in the complex plane.

34. In an ultrasonic echographic system receiving return signals wherein each return signal represents an image along a single receiving line, a method for quadrature demodulation detection of a contrast agent, comprising the steps of:

determining the in phase and quadrature components of each return signal and providing resolved complex amplitude and phase components of each return signal, wherein the in phase and quadrature components of each return signal are the resolved complex amplitude and phase components, real and imaginary of each return signal that are respectively in phase with and in quadrature phase with a reference signal and detecting a contrast agent by determining the complex difference between the resolved complex amplitude and phase components of a first return signal and the resolved complex amplitude and phase components of a second return signal, and generating a complex difference value representing the magnitude of a complex amplitude and phase difference between the resolved first and second signals due to a contrast agent, receiving three successive return signals along each receiving line wherein the second return signal and a third return signal are used to extrapolate what the first return signal would have been without the contrast agent component and to generate a decision threshold that is compared to the complex difference between the actual first return signal and the extrapolated first return signal.

35. The method for quadrature demodulation detection of a contrast agent of claim 34, wherein the step of detecting a contrast agent by operation of an extrapolation detector further comprises the step of:

receiving the first, second and third return signals and performing a complex phasor summation of the first, second and third return signals to generate a complex sum that represents the difference between the actual first return signal and an extrapolated first return signal generated from the second and third return signals and without a contribution from a contrast agent, generating a value representing the magnitude of the complex sum, generating a value representing the magnitude of the second return signal, multiplying the value representing the magnitude of the second return signal by a coefficient to generate a threshold value, and from the threshold value and the complex sum representing the difference between the actual first return signal and the extrapolated first return signal, generating an output representing whether the complex sum exceeds the threshold value.

36. The method for quadrature demodulation detection of a contrast agent of claim 35, wherein in the step of detecting a contrast agent by operation of an extrapolation detector the step of generating a complex sum by operation of a complex summer further comprises the step of:

generating a complex sum of the first, second and third return signals wherein the first and third return signals are summed with multipliers of +1 and the second return signal is summed with a −2 multiplier.

37. The method for quadrature demodulation detection of a contrast agent of claim 35, wherein the step of detecting a contrast agent further comprises the steps of:

receiving and storing the first, second and third return signals, providing as an output the first return signal, providing the second return signal as an output for the generation of the complex sum and for the generation of the value representing the magnitude of the complex sum to the complex summer, and concurrently providing the third return signal as an output for generating the complex sum.

38. The method for quadrature demodulation detection of a contrast agent of claim 34, wherein the detecting a contrast agent by operation of an extrapolation detector further comprises the steps of:

generating a first complex difference between the first and second return signals, generating a second complex difference representing the complex difference between the second and third return signals and the first complex difference, the second complex difference thereby representing the complex difference between the actual first return signal and an extrapolated first return signal generated from the second and third return signals and not including a contrast agent component, generating a value representing the magnitude of the second return signal, multiplying the value representing the magnitude of the second return signal by a coefficient to generate a threshold value, and from the threshold value and the complex sum representing the difference between the actual first return signal and the extrapolated first return signal, generating an output representing whether the complex sum exceeds the threshold value.

39. The method for quadrature demodulation detection of a contrast agent of claim 38, wherein the detecting a contrast agent by operation of an extrapolation detector further comprises the steps of:

storing the first return signal, the second return signal and the third return signal and providing as an output the first return signal for generating the first complex difference, providing the second return signal for generating the magnitude of the second return signal concurrently with providing as an output the first return signal for generating the first complex difference, storing the first complex difference between the first and second return signals and the second complex difference representing the complex difference between the second and third return signals, and providing the second complex difference between the second return signal and the third return signal as an output in conjunction with the first complex difference between the first return signal and the second return signal for generating the second complex difference.

40. The method for quadrature demodulation detection of a contrast agent of claim 34, wherein the detecting a contrast agent by operation of an extrapolation detector further comprises the steps of:

receiving the first return signal and n subsequent successive return signals and performing a complex phasor summation of the first return signal and the n subsequent successive return signals to generate a complex sum that represents the difference between the actual first return signal and an extrapolated first return signal generated from the n subsequent successive return signals and without a contribution from a contrast agent, generating a value representing the magnitude of the complex sum, generating a value representing the magnitude of the n subsequent successive return signals, multiplying the value representing the magnitude of the n subsequent successive return signals by a coefficient to generate a threshold value, and from the threshold value and the complex sum representing the difference between the actual first return signal and the extrapolated first return signal, generating an output representing whether the complex sum exceeds the threshold value.

41. The method for quadrature demodulation detection of a contrast agent of claim 40 wherein the first and n subsequent successive return signals in a given direction are interleaved with a first and n subsequent successive return signals in at least one other given direction and an extrapolated first return signal is generated for each given direction.

* * * * *